(12) United States Patent
Ellingson et al.

(10) Patent No.: US 6,285,449 B1
(45) Date of Patent: Sep. 4, 2001

(54) OPTICAL METHOD AND APPARATUS FOR DETECTION OF DEFECTS AND MICROSTRUCTURAL CHANGES IN CERAMICS AND CERAMIC COATINGS

(75) Inventors: William A. Ellingson, Naperville; Judith A. Todd, Hinsdale; Jiangang Sun, Westmont, all of IL (US)

(73) Assignee: University of Chicago, Chicago, IL (US)

( * ) Notice: Subject to any disclaimer, the term of this patent is extended or adjusted under 35 U.S.C. 154(b) by 0 days.

(21) Appl. No.: 09/330,727

(22) Filed: Jun. 11, 1999

(51) Int. Cl.⁷ .................................................. G01N 21/00
(52) U.S. Cl. ........................... 356/237.1; 356/369
(58) Field of Search .................. 356/237.1, 364, 356/369, 338, 371, 237.2; 250/559.09, 559.42, 559.45, 559.46, 559.48, 225

(56) References Cited

U.S. PATENT DOCUMENTS

| | | | |
|---|---|---|---|
| 4,286,293 | * 8/1981 | Jablonowski | 358/199 |
| 4,725,139 | * 2/1988 | Hack et al. | 356/237.1 |
| 5,149,978 | * 9/1992 | Opsal et al. | 356/335 |
| 5,426,506 | 6/1995 | Ellingson et al. | 356/369 |
| 5,689,332 | 11/1997 | Ellingson et al. | 356/237 |

OTHER PUBLICATIONS

Wave Optics Inc. informational report on "Polarization Maintaining Fiber," pp. 12–13, from www.Waveoptics.com website, undated.

* cited by examiner

Primary Examiner—Hoa Q. Pham
(74) Attorney, Agent, or Firm—Emrich & Dithmar

(57) ABSTRACT

Apparatus detects defects and microstructural changes in hard translucent materials such as ceramic bulk compositions and ceramic coatings such as after use under load conditions. The beam from a tunable laser is directed onto the sample under study and light reflected by the sample is directed to two detectors, with light scattered with a small scatter angle directed to a first detector and light scattered with a larger scatter angle directed to a second detector for monitoring the scattering surface. The sum and ratio of the two detector outputs respectively provide a gray-scale, or "sum" image, and an indication of the lateral spread of the subsurface scatter, or "ratio" image. This two detector system allows for very high speed crack detection for on-line, real-time inspection of damage in ceramic components. Statistical image processing using a digital image processing approach allows for the quantative discrimination of the presence and distribution of small flaws in a sample while improving detection reliability. The tunable laser allows for the penetration of the sample to detect defects from the sample's surface to the laser's maximum depth of penetration. A layered optical fiber directs the incoming laser beam to the sample and transmits each scattered signal to a respective one of the two detectors.

10 Claims, 14 Drawing Sheets

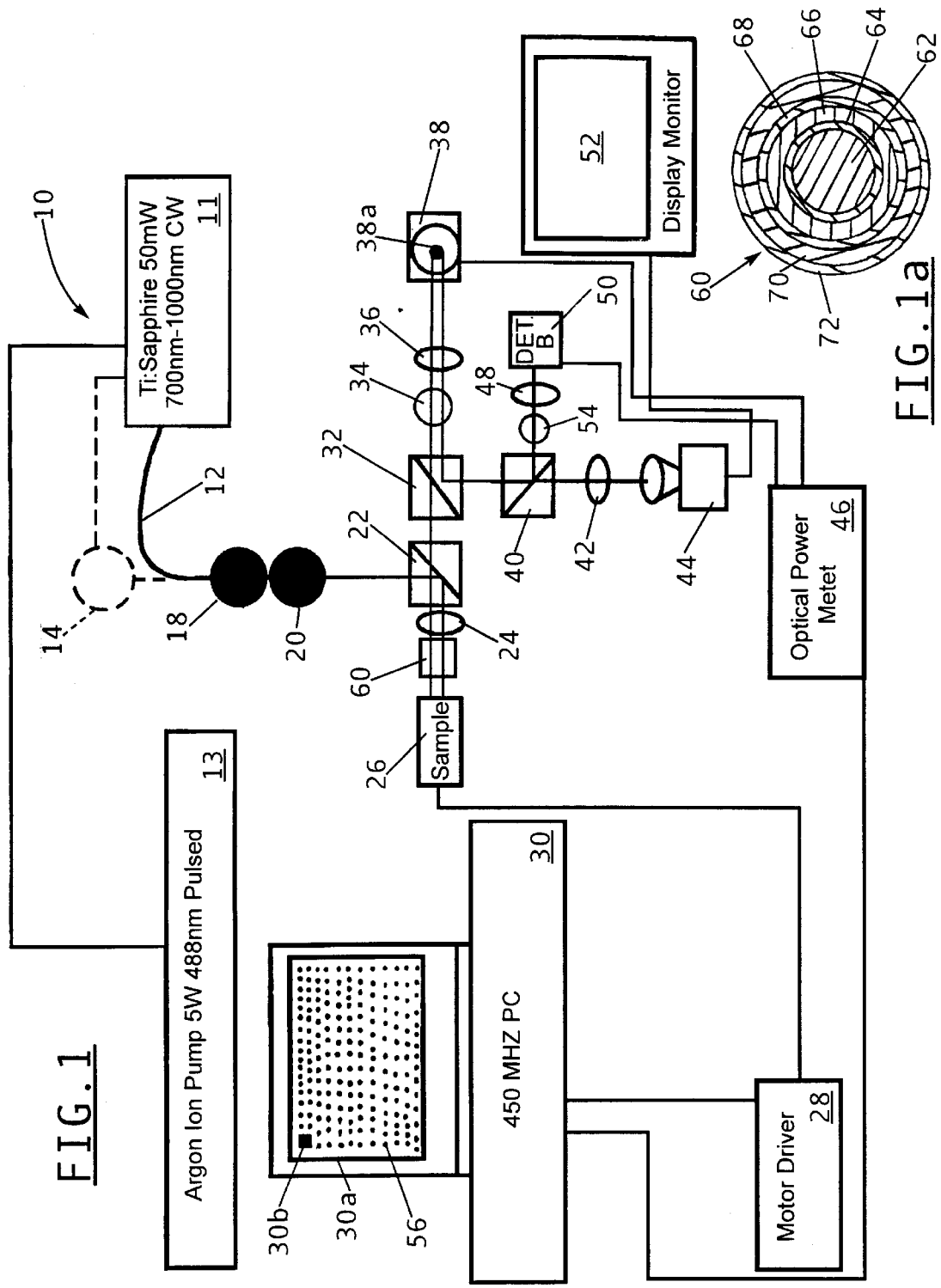

Gauge Section, Side 1

.1403

.1122

Head Section, Side 1

Coefficient of Variance $C_v$

Gauge Section, Side 2

.1526

.1102

Head Section, Side 2

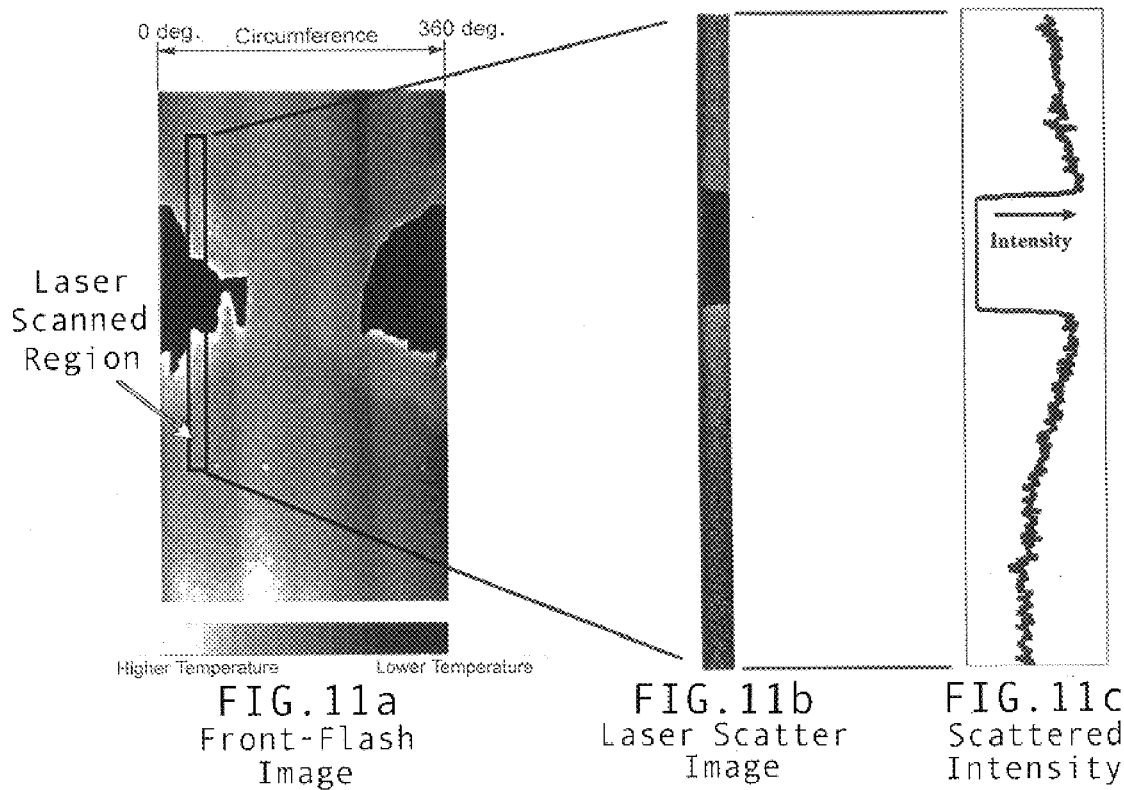
FIG.11a Front-Flash Image
FIG.11b Laser Scatter Image
FIG.11c Scattered Intensity

OPTICAL METHOD AND APPARATUS FOR DETECTION OF DEFECTS AND MICROSTRUCTURAL CHANGES IN CERAMICS AND CERAMIC COATINGS

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

FIELD OF THE INVENTION

This invention relates generally to an optical instrument and method for the inspection of ceramic materials and is particularly directed to the automated, real-time detection of defects and microstructural changes in ceramic and ceramic composite materials in bulk form or as a coating.

BACKGROUND OF THE INVENTION

Ceramic and ceramic composite material components and ceramic coated components are attractive candidate materials for improved efficiency power systems over their metal counterparts because of the lighter weights and higher strengths at elevated temperatures of the ceramic-based components. For example, monolithic silicon nitride vanes and turbine blades and silicon carbide composite combustor liners are currently being evaluated in high performance gas turbine engines. Highly stressed areas of ceramic components, such as turbine blades, include the near-surface regions, particularly the blade trailing edges. Accumulation of elevated temperature damage and microstructural changes over time in these near surface regions may lead to premature failure.

When ceramic and ceramic composite materials and ceramic coatings are loaded at temperatures above approximately one-third of their melting/ablation temperatures, these materials and coatings undergo creep phenomena. These creep phenomena may include: development of cavities or voids along grain boundaries, development of voids in grain boundary glassy phases, formation of wedge cracks at grain boundary triple points, linkage of cavities to form grain facet sized cracks which then link to form microcracks, and linkage of microcracks to form macrocracks until failure occurs when a critical flaw size is reached. Microstructural changes such as grain growth, phase changes, dissolution and precipitation phenomena, oxidation, scaling and spalling may also occur. Coatings subjected to thermal and mechanical stresses may develop internal cracks as well as delaminations at the coating substrate interfaces, leading ultimately to spalling.

Structural ceramics, e.g., silicon nitride and silicon carbide ceramic and ceramic composite materials, are increasingly being used for high temperature gas turbine applications in not only vanes and turbine blades, but also combustor liners because of their high thermal stabilities and elevated temperature strengths. In these types of applications, the critical regions of a component experiencing the highest stresses are frequently the surface and near-surface regions to a depth on the order of 200–300 microns. Increased depths to approximately 500 microns are also of interest in the structural analysis of these ceramic-based materials. The presence of large stresses on the surface and in near-surface regions can lead to the development of creep cavities and wedge cracks which ultimately link to form microcracks until a dominant microcrack results in rupture. The detection of damage accumulation in structural ceramics, particularly $Si_3N_4$ and SiC creep tested in air is extremely difficult. Periodic surface inspection of $Si_3N_4$ components undergoing high temperature loading reveals that oxidation products and the formation of glassy phases frequently obscure the presence of surface flaws. Indeed, attempts to use hardness indentations to measure the development of creep strains in creep flexure bars have proved unsuccessful due to glassy phases obscuring the reference indents during the creep test.

The present invention addresses the aforementioned limitations of the prior art by allowing for the periodic "imaging" of a ceramic component in its operating environment, i.e., as installed in an operating component of a machine, and allows the material at the surface as well as below the surface to be assessed for damage. This inventive method and apparatus is particularly adapted for use in detecting defects and microstructural changes in ceramic and ceramic composite materials in bulk form as well as in ceramic coatings such as used in nozzles, vanes, rotor blades and combustor lines used in high temperature gas turbine applications.

OBJECTS AND SUMMARY OF THE INVENTION

Accordingly, it is an object of the present invention to detect defects and microstructural changes in ceramic and ceramic composite materials on a real-time basis using an automated approach.

It is another object of the present invention to detect surface and subsurface defects and microstructural changes that develop in ceramic and ceramic composite materials either in bulk form or in the form of a coating when exposed to high temperatures and constant, cyclic, random, residual or shock loading.

Yet another object of the present invention is to use a combination of optical microscopy and elastic optical scattering to detect surface and subsurface creep damage in ceramic and ceramic composite materials and coatings during on-site inspection of the ceramic component without removing the component from the item in which it is installed.

A further object of the present invention is to increase the accuracy and reliability of detection of the presence and distribution of small surface and subsurface flaws in ceramic bulk compositions and ceramic coatings using plural detectors and statistical image processing employing quantative discrimination.

This invention contemplates apparatus for detecting and characterizing surface and subsurface defects and microstructural changes in translucent ceramic-based materials and coatings, the apparatus comprising a tunable wavelength laser providing an output beam of high intensity light; optical means for directing the output beam onto a specimen of a ceramic-based material or coating and for receiving light scattered from the specimen, the optical means including polarizing means for controlling the polarization of the output beam prior to incidence upon the specimen, where the output beam wavelength allows the beam to penetrate the specimen from its surface to a given depth of the specimen, and wherein the given depth corresponds to the upper wavelength limit; a detector system with means for receiving light scattered over two scattering angles from the localized area of the specimen's surface or subsurface being investigated and providing an output signal representing light scattered from the localized area; two detectors for receiving light scattered over two scatter angles for providing two output signals representing light scattered from two scatter angles; and display processing means coupled to the first and second detectors for processing the first and second output signals and visually displaying defects and microstructural changes on and below the surface of the specimen.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 1 is a simplified combined block and schematic diagram of apparatus for detecting defects and microstructural changes in ceramic and ceramic composite materials and ceramic coatings in accordance with the principles of the present invention;

FIG. 1a is a sectional view of a layered optical fiber for carrying the laser beam incident on a specimen under study as well as the light scattered from the specimen;

FIGS. 3a, 3b and 3c respectively show the optical, sum and ratio images after polishing away an average of 35 microns from the surface of the specimen shown in FIG. 2a;

FIGS. 4a, 4b and 4c respectively show the optical, sum and ratio images after polishing away an average of 135 microns from the surface of the specimen shown in FIG. 2a;

FIGS. 5a, 5b and 5c respectively show the optical, sum and ratio images after polishing away an average of 275 microns from the surface of the specimen shown in FIG. 2a;

FIGS. 6a, 6b and 6c respectively show the optical, sum and ratio images after polishing away an average of 435 microns from the surface of the specimen shown in FIG. 2a;

FIGS. 11a–11c respectively show a thermal image, a laser scatter sum image, and intensity profiles of the laser sum image of a combustor liner section that spalled during service.

DETAILED DESCRIPTION OF THE PREFERRED EMBODIMENTS

Figure 2A:
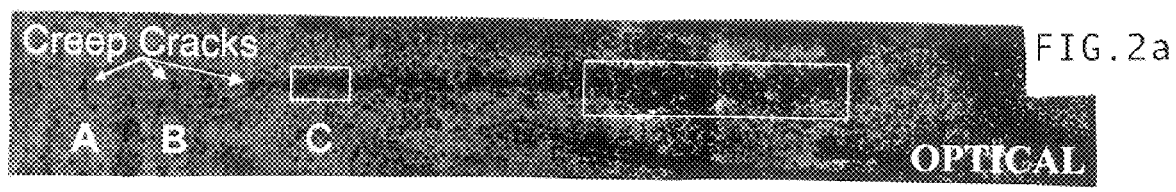
FIGS. 2a, 2b and 2c are specimen images of the surface of $Si_3N_4$—$6Y_2O_3$—$2Al_2O_3$ that has been subjected to elevated temperatures respectively illustrating the optical, sum and ratio images as used in the present invention.

Referring to FIG. 1, there is shown a simplified combined block and schematic diagram of optical apparatus 10 for detecting defects and microstructural changes in ceramic and ceramic composite materials and ceramic coatings in accordance with the principles of the present invention. The optical apparatus 10 includes a Ti:Sapphire tunable laser 11 having a nominal power output of 50 mW and a tunable wavelength range of 700–1000 nm CW. The beam from an Argon ion pump laser 13 is provided to the tunable Ti:Sapphire laser 11 for tuning the laser over the aforementioned wavelength range. The Argon ion pump laser 13 is operated in a pulsed mode at a wavelength of 488 nm and a 5 W output power.

In a preferred embodiment, the beam from the tunable laser 11 is provided via an optical fiber 12 or an optical fiber array to the combination of an attenuating beam-splitter 18 and a half-wave plate 20. The beam from the tunable laser 11 may also be provided to the attenuating beam-splitter 18 and half-wave plate 20 combination by means of a mirror 14 (shown in the figure in dotted line form), but the use of the aforementioned optical fiber 12 provides advantages over the mirror approach which are described in detail below. In some cases it may be desirable to limit the fixed power of the tunable laser's output beam. Thus, the attenuating beam-splitter 18 may include a partially silvered mirror for attenuating the power of the laser beam. The attenuating beam-splitter 18 thus permits the tunable laser 11 to be used in applications requiring reduced laser beam power. The half-wave plate 20 permits the polarization of the output beam from the tunable laser 11 to be adjusted as desired prior to irradiation of a ceramic sample 26. Thus, if horizontal polarization is required for ceramic sample 26 irradiation, the half-wave plate 20 may be used to change vertical polarization of the output beam from the tunable laser 11 to horizontal polarization. If the polarization of the output beam of the tunable laser 11 is the same as that required for the beam irradiating the ceramic sample 26, half-wave plate 20 is not necessary.

The polarized and possibly attenuated laser beam processed by the attenuating beam splitter 18 and half-wave plate 20 is then provided to a first polarizing beam-splitting cube 22 which directs the beam onto the ceramic sample 26 via a positive focusing lens 24 and a multi-layer polarization maintaining optical fiber 60. The polarization maintaining optical fiber 60 is described in detail below. Light reflected from the surface of the ceramic sample 26 undergoes essentially no change in polarization and is directed back to the first polarizing beam-splitting cube 22 via optical fiber 60 and focusing lens 24. Because light scattered from below the surface of defective ceramic sample 26 is randomly polarized, part of the subsurface scattered light is directed from the ceramic sample back through the multi-layer optical fiber 60 to the polarizing beam-splitting cubes 22 and 32. Part of the light scattered by the ceramic sample 26 is scattered over a small angle and this portion of the scattered beam is transmitted by the first polarizing beam splitting cube 22 to a second polarizing beam-splitting cube 32. The scattered light from the ceramic sample 26 does two things: part passes through the second polarizing beam-splitting cube 32 and part is reflected to beam-splitting cube 40. The part passing through beam-splitting cube 32 is directed through a first quarter-wave plate 34, a positive focusing lens 36, and thence to a first detector 38. The first detector 38 includes a polished stainless steel pinhole aperture 38a approximately 100 microns in diameter. The scattered light directed through the pinhole aperture 38a is recorded via the first detector 38 and a corresponding signal is provided to one input of an optical power meter 46. The light directed through the pinhole aperture 38a is light scattered over a small scattering angle from a small area of the ceramic sample 26 representing the specific area under investigation. The polished stainless steel reflector which includes the aforementioned pinhole aperture 38a reflects a portion of the scattered light back to the second polarizing beam-splitting cube 32 which then reflects a portion of this reflected beam to a 50/50 beam-splitting cube 40. The part passing to the 50/50 beam-splitting cube 40 reflects a portion of the beam through the combination of a second quarter-wave plate 54 and a positive focusing lens 48 and to a second detector 50. The portion of the beam directed to the second detector 50 represents light scattered over a wider angle from a portion of the ceramic sample 26 disposed about the specific area under investigation. An output signal representing the light scattered from the portion of the ceramic sample 26 disposed about the area of investigation is provided to a second input of the optical power meter 46. Thus, light provided to the first detector 38 is light reflected over a small angle through the narrow numerical pinhole aperture 38a which is scattered from the specific area under investigation. Light provided to the second detector 50 is light scattered over a larger angle from the ceramic sample 26 disposed about the specific area under investigation. The optical power meter 46 converts the optical outputs from the first and second detectors 38,50 and provides these signals to a computer 30 which includes a video display terminal 30a. The ceramic sample 26 is coupled to a motor driver 28 which operates under the control of computer 30 for displacing the ceramic sample along X-, Y-, and Z-axes to permit the laser beam to scan the sample.

Referring to FIG. 1a, there is shown a sectional view of the polarization maintaining optical fiber 60 which directs the incident laser beam onto and receives scattered light from the ceramic sample 26. Polarization maintaining optical fiber 60 includes an inner optical fiber 62 which carries the laser beam generated by the tunable laser 11 and directs the beam onto the ceramic sample 26. Concentrically disposed about the inner optical fiber 62 is an inner reflective layer 64. Concentrically disposed about the inner reflective layer 64 is an intermediate optical fiber 66 which receives the scattered light scattered over a small angle from the ceramic sample 26 and provides this scattered light to the first polarizing beam-splitting cube 22 via focusing lens 24. Concentrically disposed about the intermediate optical fiber 66 is an outer reflective layer 68. Concentrically disposed about the outer reflective layer 68 is an outer optical fiber 70 which receives the scattered light reflected over larger angles and provides this scattered light to the first polarizing beam-splitting cube 22 via focusing lens 24. The reflective layers confine the transmitted light to the optical fibers and prevent interference with the optical signals. An outer sheath is disposed about the outer optical fiber 70. Polarization maintaining optical fiber 60 is conventional in design and operation in the present invention and is well known to those skilled in the relevant arts. Similarly, a suitable lens on the end of the polarization maintaining optical fiber 60 for directing the laser beam onto the ceramic sample 26 and receiving the scattered light reflected from the sample is well known to those skilled in the relevant arts and is thus not described further herein.

A portion of the scattered light provided to the 50/50 beam-splitting cube 40 is transmitted by the cube via a positive focusing lens 42 to a charge coupled device (CCD) camera 44. The CCD camera 44 provides a signal representing the scattered light transmitted by the 50/50 beam-splitting cube 40 to a display monitor 52 for providing a real-time video image of the scattered light. In general, the beam directed to the CCD camera 44 is used to monitor the scattering surface of the ceramic sample 26.

One of the primary advantages of using the optical fiber 12 is to permit the optical apparatus 10 to detect defects and microstructural changes in ceramic and ceramic composite materials and ceramic coatings of a component without removing the component from the apparatus or machine in which it is installed. More specifically, the typical tunable laser 11 is bulky and rather large in size, which limits access of its laser beam to an installed component. The optical components including the attenuating beam-splitter 18, half-wave plate 20, first and second polarizing beam-splitting cubes 22, 32, first and second quarter-wave plates 34,54, the 50/50 beam-splitting cube 40 and associated focusing optics can be packaged in a very small volume, e.g., in 6–7 cubic inches. This compact optical package connected to the tunable laser 11 via the optical fiber 12 allows the laser beam to be directed onto the ceramic sample 26 which may be in a confined space affording limited accessibility.

The two detector approach adopted by the optical apparatus 10 of the present invention provides information regarding the size and type of a particular defect. A small, confined defect will provide scattered light having a limited scatter angle to the first detector 38. A defect with a larger scatter angle will diffuse the light scattered from the sample over a greater angle of divergence and will provide a larger scattered light input to the second detector 50. The relationship between the respective outputs of the first and second detectors 38,50 provided to the optical power meter 46 can thus be used to determine the size of the defect. These two inputs to the optical power meter 46 can also be used to ascertain the particular type of detected defect or microstructural change.

Evaluation of a ceramic component requires separation of the combined surface and subsurface scattering components. This can be accomplished by considering the polarization states of the illumination and detection paths. For surfaces that are sufficiently smooth to permit only a single interaction of each photon with the surface, the polarization of the surface scatter will be only mildly changed from that of the incident beam. However, if the subsurface scattering population is sufficiently dense, then each photon will undergo multiple interactions, resulting in a more significant polarization of the scattered light. As a result, careful selection of the incident and detector polarization permits the effective separation of the surface and subsurface scattering components.

In accordance with another aspect of the present invention, the computer terminal display 30a includes a plurality of pixels 56 arranged in a matrix array on the display screen. In a typical PC terminal video display, the array consists of 512×512 pixels. In accordance with this aspect of the invention, each of the pixels 56 is assigned a number representing a gray scale value of the video image detected by the first and second detectors 38,50 and processed by the optical power meter 46. Statistically analyzing the gray scale values of the pixels 56 on the terminal display 30a allows one to calculate statistical parameters of the gray scale of the video image such as mean, standard deviation, skewness, etc. The skewness, for example, represents the deviation of the gray scale of all of the pixels 56 from a normal distribution. From the gray scale values of the pixels 56, one can also calculate the mean gray scale, i.e., 50% of the pixels having a lighter shade and 50% of the pixels having a darker shade than the mean gray scale value. From these and other statistical values which can be calculated from the gray scale value assigned to each pixel, parameters such as the coefficient of skewness and the coefficient of variation can be calculated. Using either the coefficient of skewness or the coefficient of variation, a threshold gray scale value may be assigned such that gray scale values greater than this threshold value represent a defect and gray scale values less than this threshold value represent the absence of a defect. In this manner, computer 30 may be programmed to process the outputs of the optical power meter 46 to provide automatic detection of defects and an automatic indication of defect detection such as by a visual indication 30b on the video display 30a or an audio signal.

Figure 2B:
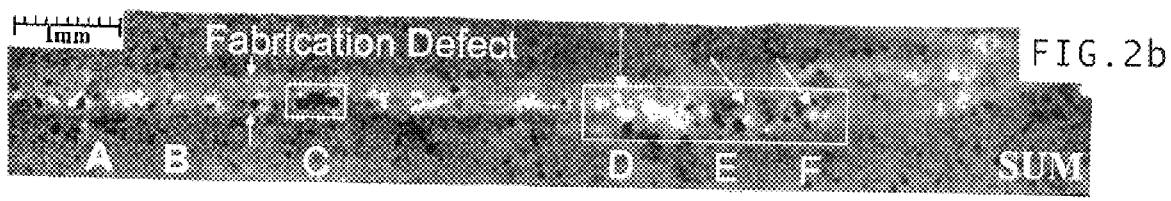
Figure 2C:
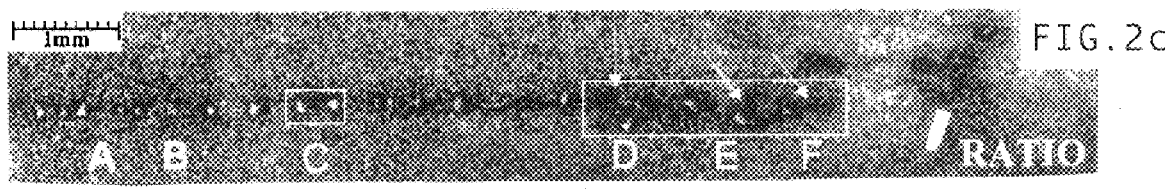

Referring to FIGS. 2a, 2b and 2c, there are shown images of the surface of a $Si_3N_4$—$6Y_2O_3$—$2Al_2O_3$ specimen that has been subjected to elevated temperatures respectively illustrating the optical, sum and ratio images as provided by the present invention. The specimen of $Si_3N_4$—$6Y_2O_3$—$2Al_2O_3$ was subjected to elevated temperature four point flexure creep testing for 5.16 hours at 1400° C. and a stress of 41.5 MPa. The optical image of FIG. 2a shows an oxidized surface with a row of deep cracks along the centerline of the specimen. The sum image of FIG. 2b shows that the creep cracks are associated with a light gray band of material approximately 0.5 mm in width. The light gray band of material cannot be distinguished in the unpolished surface shown in FIG. 2a as the band is obscured by an oxide film. Subsequent polishing reveals that this band is a fabrication defect in the specimen being studied. The intense white patches in the sum image shown in FIG. 2band corresponding black regions in the ratio image of FIG. 2c indicate the presence of subsurface damage, some of which extends as far as 500 microns below the specimen surface. In general, the sum image exhibits greater sensitivity to surface defects and microstructural changes and is better at recognizing certain types of anomalies. The ratio image, on the other hand, is more sensitive to subsurface defects and microstructural changes and provides greater detail within, rather than on, the surface of the specimen under investigation.

Figure 3A:
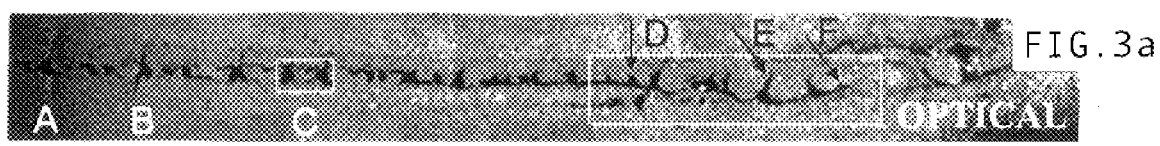
Figure 3B:
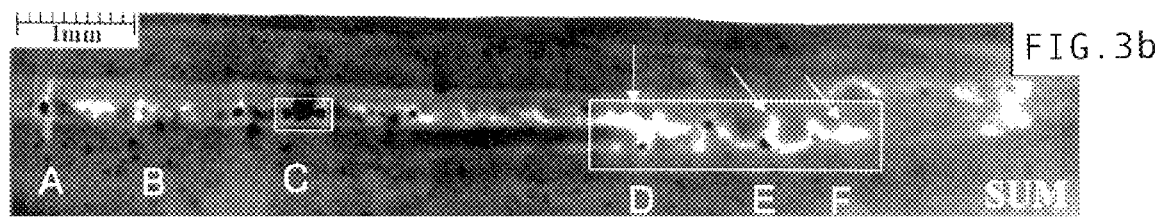
Figure 3C:
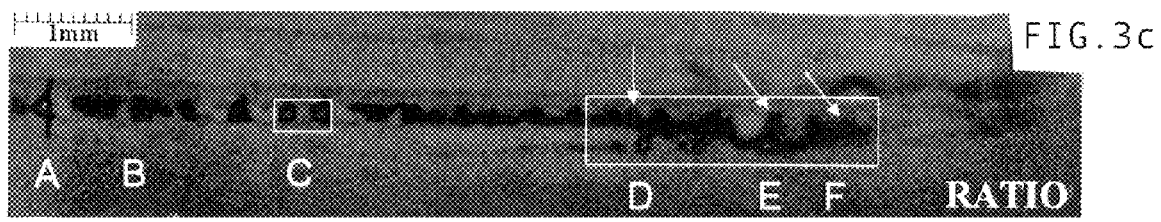

FIGS. 3a, 3b, and 3c respectively show the optical, sum and ratio images after polishing away an average of 35 microns from the surface of the specimen shown in FIG. 2a. FIG. 3a shows: (a) the fabrication defect also shown in FIG. 2b; (b) a 450 micron long and <30 micron wide defect at A, which FIGS. 3b and 3c indicate persists below the polished surface; (c) two holes connected by fine cracks in box C; and (d) flaws D,E and F ranging from 50–250 microns in length. FIGS. 3b and 3c indicate that these flaws open up in removing more material such as by polishing.

Figure 4A:
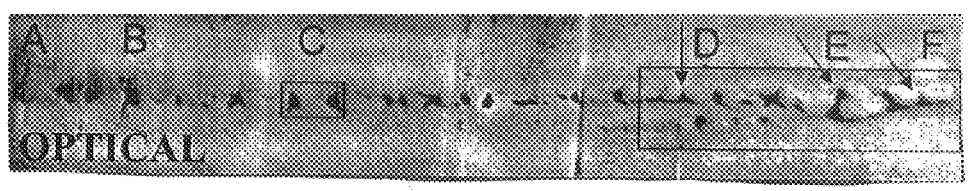
Figure 4B:
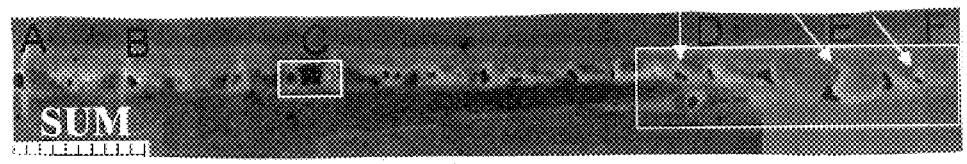
Figure 4C:
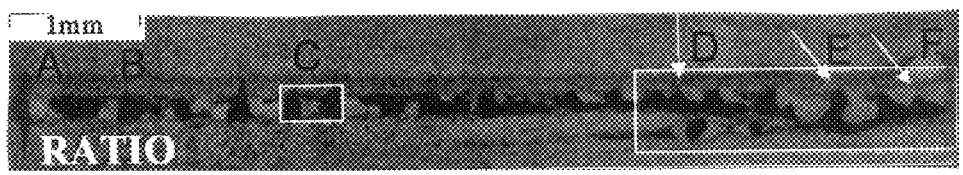

FIGS. 4a, 4b and 4c respectively show the optical, sum and ratio images after polishing away an average of 135 microns from the surface of the specimen shown in FIG. 2a. FIG. 4a shows the previously described 450 micron defect at A as well as the flaw at B which is 350 microns in length. FIG. 4a also shows holes in box C which have opened up to 150 microns in size, as well as a 100 micron diameter hole at the tip of point E. The fabrication defect is still clearly visible in the figures.

Figure 5A:
Figure 5B:
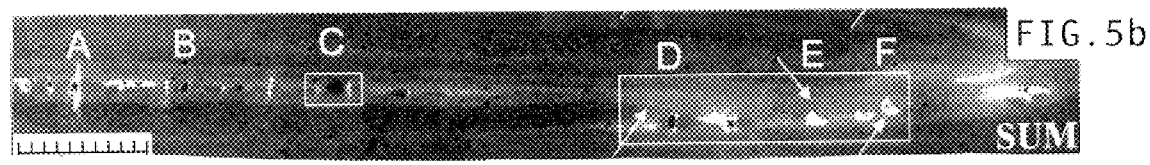
Figure 5C:
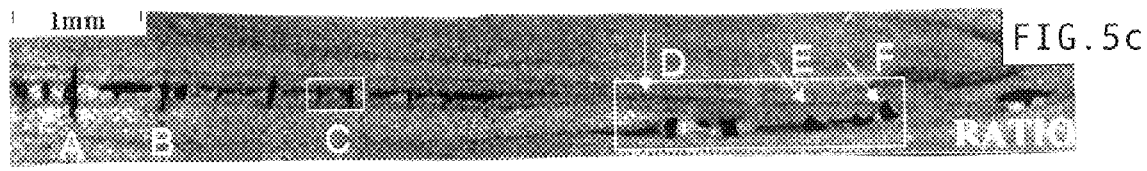

FIGS. 5a, 5b and 5c respectively show the optical, sum and ratio images after polishing away an average of 275 microns from the surface of the specimen shown in FIG. 2a. FIGS. 5a, 5b and 5c show that significant creep damage has been removed by the polishing operation. Although the defect at A is not clearly visible on the optical micrograph of FIG. 5a, both sum and ratio images provide a strong indication of its presence as shown in FIGS. 5b and 5c. The sum and ratio images of the defect at A indicate that it is 300 microns in length after the removal of 350 microns (which is not shown in the figures). Defects at B, C, D, E, and F in FIGS. 5a–5c are now much smaller than those images which are closer to the surface of the specimen as previously described. However, there is a strong indication in these figures of additional subsurface damage at E.

Figure 6A:
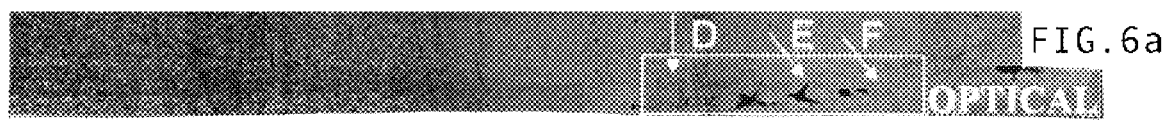
Figure 6B:
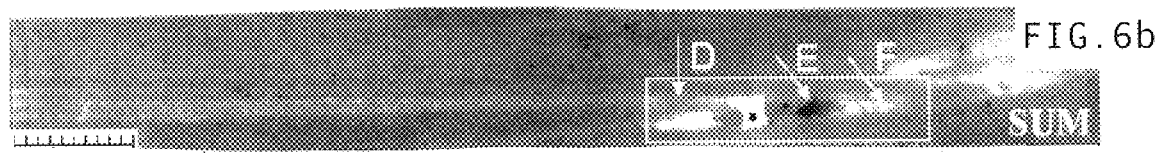
Figure 6C:
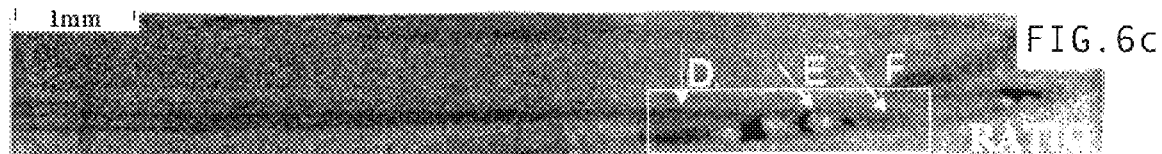

Referring to FIGS. 6a, 6b and 6c, there are respectively shown the optical, sum and ratio images after polishing away an average of 435 microns from the surface of the specimen shown in FIG. 2a. Removal of 435 microns confirms that the flaw located at E increased in size in proceeding deeper into the specimen as shown in FIG. 6a. FIGS. 6b and 6c provide only a hint of the flaw located at previously described point A, which flaw completely disappeared after 500 microns was removed from the surface of the specimen by polishing. The majority of the creep damage had been removed by polishing to a depth of 435 microns. Although the fabrication defect was narrower at the increased depth of FIGS. 6a–6c, this defect was nevertheless still visible in these figures. In summary, FIGS. 2a through 6c show that a defect indicated as 450 microns long by <30 microns wide in the sum image of the oxidized and crept surface persisted to a depth of 435 mircons below the surface of the specimen. Defects <50 microns in size could be detected to a depth of 200 microns. The fabrication defect discussed above was clearly indicated in FIG. 2b and persisted to a depth of 435 microns below the surface of the specimen.

The early stages of creep damage may result in distributions of cavities less than 5 microns in size, at grain boundaries oriented perpendicular to a tensile stress. While such cavities will influence the subsurface scattering of linearly polarized light, statistical processing of the images obtained using the present invention can be used to identify such damage. The influence of cavitation on elastic optical scattering can be investigated by comparing sum and ratio images from the gauge and head sections of, for example, a tensile creep specimen. Both sections will be exposed to the same temperature, but the head section will experience a much lower stress than the gauge section.

Figure 7A:
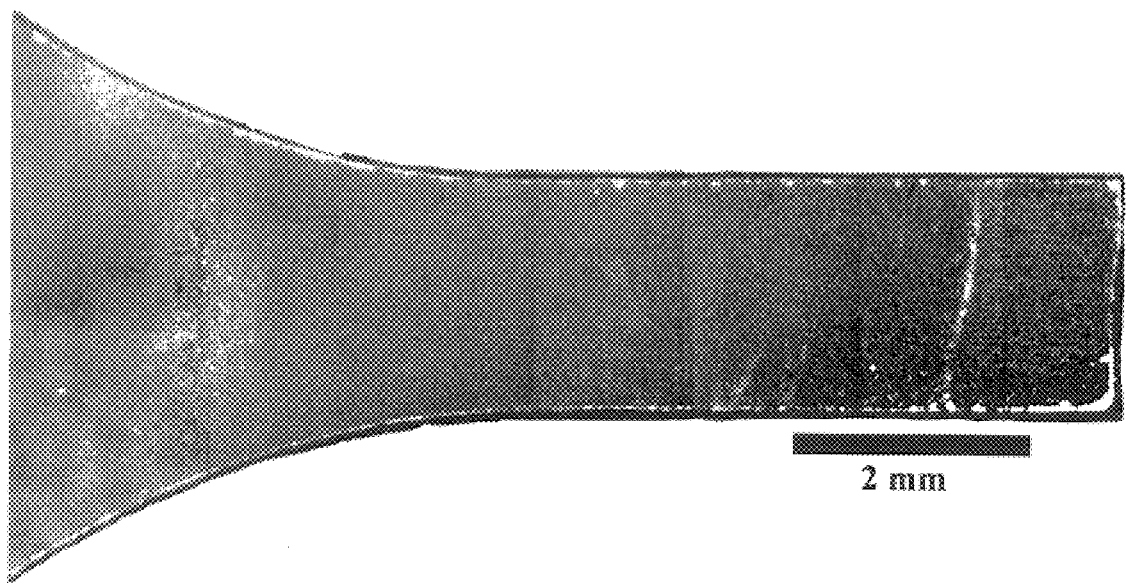
FIGS. 7a and 7b respectively show the optical and sum images of a $Si_3N_4$ (NGK SN88) creep specimen tested at 1400° C. and a stress of 200M Pa.
Figure 7B:
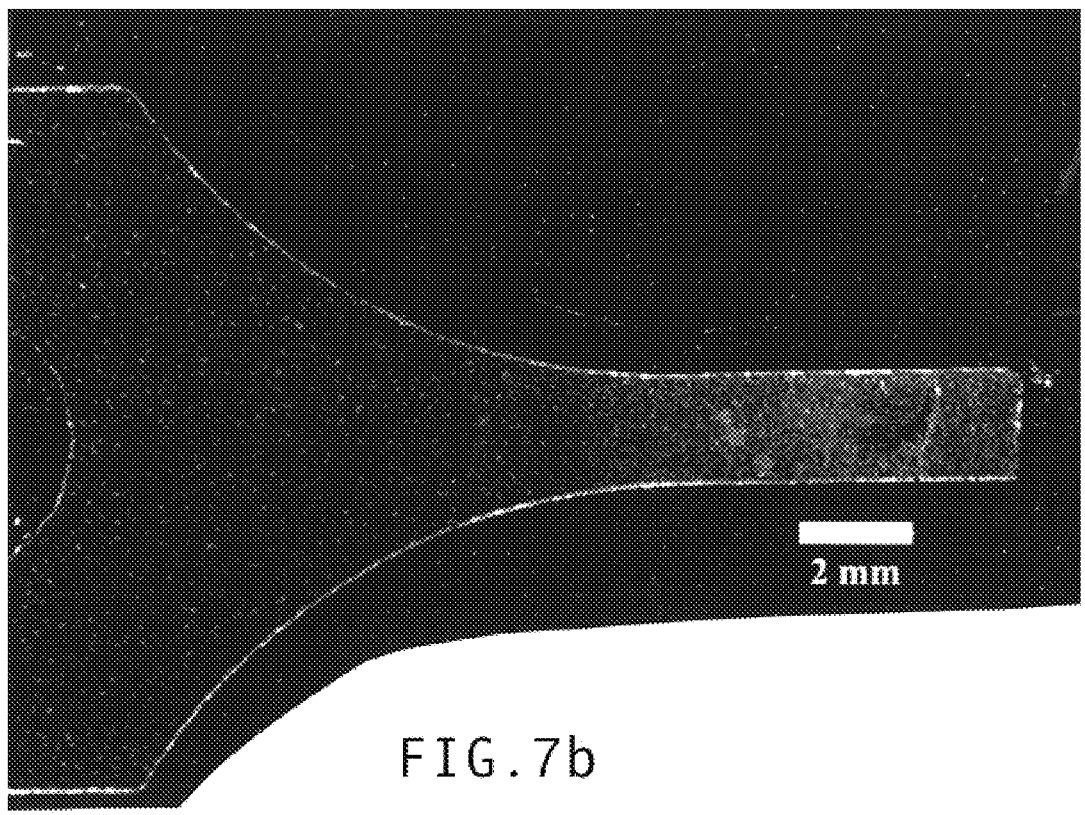
Figure 8A:
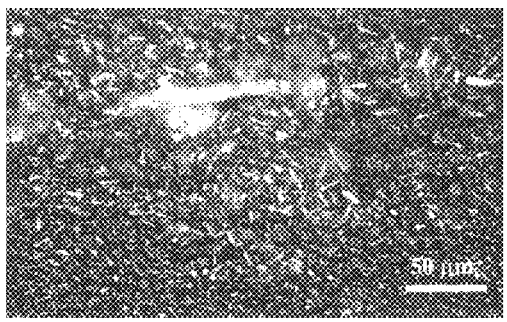
FIGS. 8a and 8b respectively show the optical images of the $Si_3N_4$ (NGK SN88) specimen shown in FIG. 7a under high magnification.
Figure 8B:
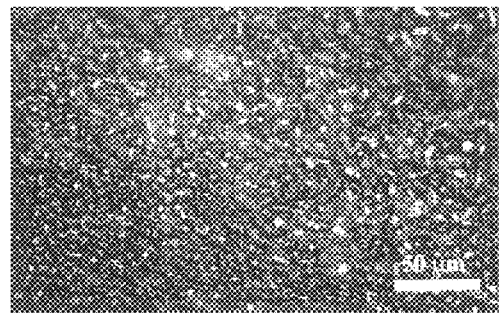

The influence of cavitation on elastic optical scattering can be seen in FIGS. 7a and 7b which show the optical and sum images, respectively, of a $Si_3N_4$ (NGK SN88) creep specimen which was tested at 1400° C. and a stress of 200 MPa. Both statistically processed images of FIGS. 7a and 7b show a light band across the gauge section and light patches within the gauge section of the specimen. The high magnification optical micrographs of the SN88 tensile specimen shown in FIGS. 8a and 8b reveal that these bands contain small cracks associated with regions containing $Si_3N_4$ whiskers that had also experienced grain growth.

Figure 9A:
FIGS. 9a, 9b and 9c,9d respectively compare the sum images from the gauge and head sections of side 1 and side 2 of the SN88 tensile specimen shown in FIGS. 7a, 7b and 8a, 8b.
Figure 9B:
Figure 9C:
Figure 9D:

FIGS. 9a and 9b compare the sum images from the head and gauge sections of side 1 of the SN88 tensile specimen, while FIGS. 9c and 9d compare the sum images on the head and gauge sections of side 2 of the specimen. While it is difficult to distinguish differences between the images of the two sides of the SN88 tensile specimen by the naked eye, use of the statistical digital image processing employed in the present invention show significantly higher coefficients of variance for the gauge sections than the head sections of the tensile creep specimen shown in FIGS. 9a–9d. The optical images shown in FIGS. 7a and 7b as well as in FIGS. 9a–9d illustrate that creep cavitation damage can be identified by statistical processing of elastic optical scattering images. In addition, it can be seen that from these results that the surface images can be used to identify regions with microstructural changes such as the development of whisker $Si_3N_4$ and grain growth.

The results described above were obtained using a continuous wave laser with a wavelength of 630 nm. The penetration depth of laser light increases as a function of wavelength. Penetration to a depth of 800 microns is attainable for silicon nitride ceramics with a laser wavelength of 850 nm. Thus, the optical method of the present invention is capable of detecting elevated temperature damage in the leading edges of silicon nitride turbine blades which are approximately 800 microns thick.

Figure 10A:
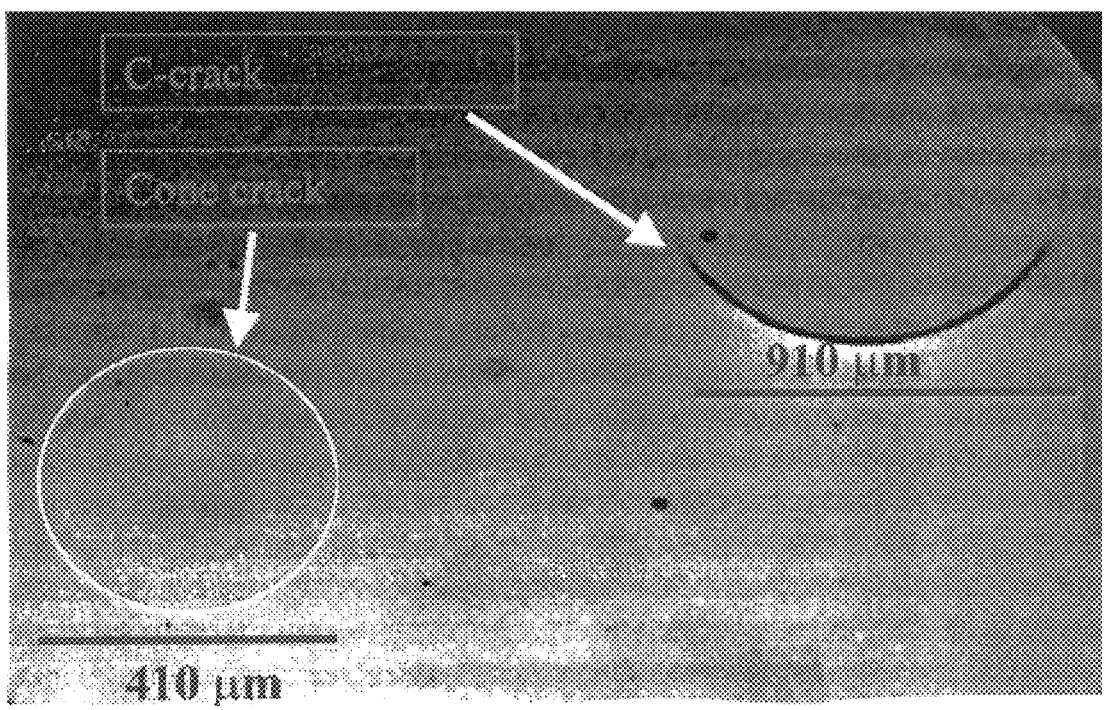
FIGS. 10a–10c show the improvement in resolution of subsurface flaws in a NIST control sample showing a C-crack on the right and a cone crack on the left by increasing the laser wavelength from 633 nm to 850 nm.
Figure 10B:
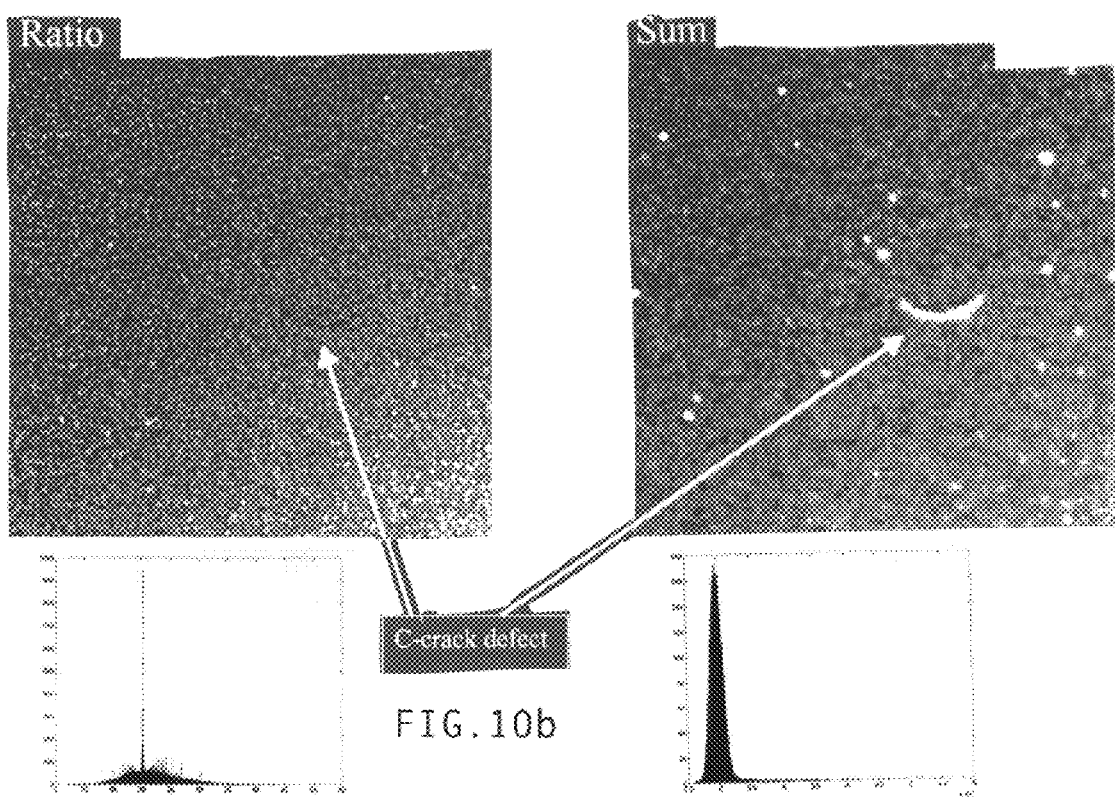
Figure 10C:
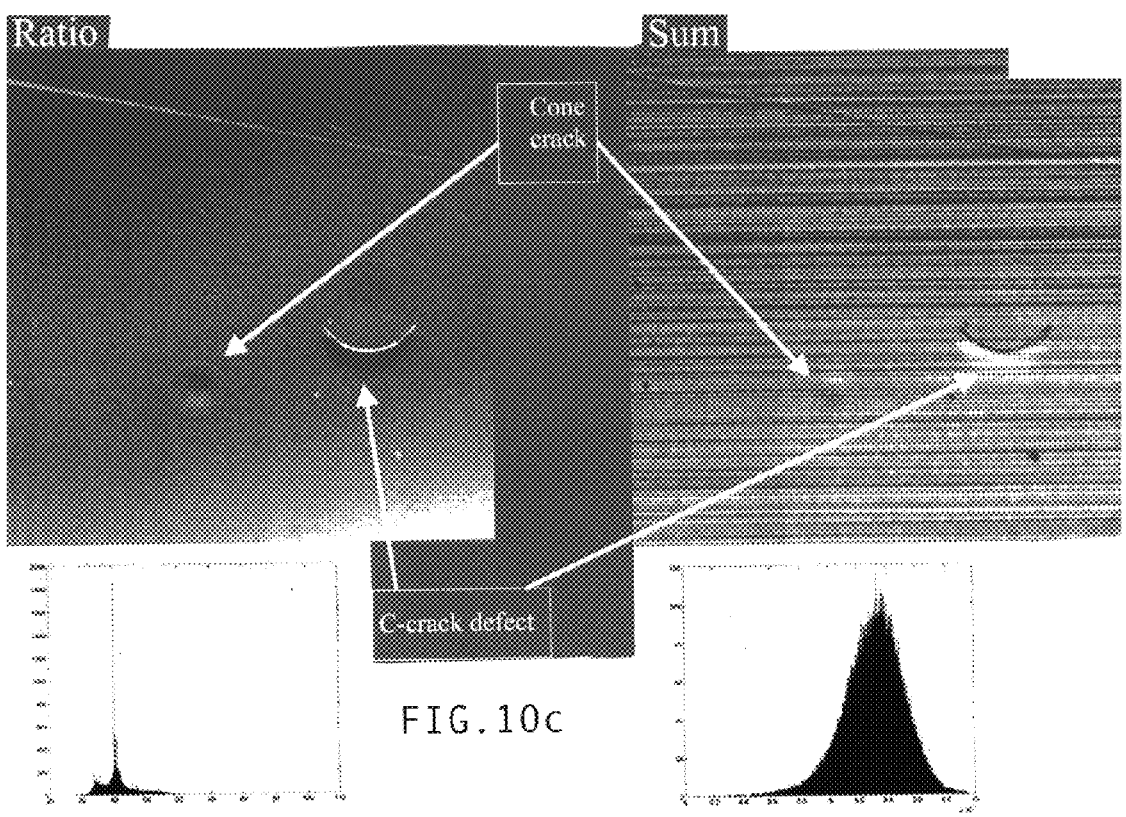

Referring to FIGS. 10a–10c, there is shown the improvement in resolution of subsurface defects in a NIST control sample by increasing the laser wavelength from 630 nm to 850 nm. FIG. 10a is an optical micrograph of the NIST control sample showing a C-crack on the right and an cone crack on the left. The sum and ratio images provided with a laser wavelength of 633 nm identify the C-crack on the right but not the cone crack on the left as shown in FIG. 10b. When the laser wavelength is increased to 850 nm, both the C-crack and the cone crack are clearly visible as shown in FIG. 10c. The C-crack appeared longer in FIG. 10c, indicating a greater penetration depth.

Thermal and environmental barrier coatings of, for example, zirconia-based and mullite coatings are finding increased application for protection of metallic substrates at elevated temperatures. These coating systems are being developed for use in such apparatus as gas turbines, hot-gas filters, and microturbines. Degradation of these types of coatings occurs through oxidation, leading to the development of cracks within the coating and delamination at the coating-substrate interface. Eventually, the cracks and delamination lead to spalling of the coating and loss of protection for the underlying substrate. The elastic optical scattering approach of the present invention provides a non-destructive in-situ approach for evaluating coating integrity.

With references to FIGS. 11a–11c, there is shown the analysis of a combustor liner section that has spalled during service. FIG. 11a is an infrared wavelength (3–5 microns) thermal image of the combustor liner section with the black areas representing the spalled region, the light grey ring around the spalled areas representing delamination, and the medium grey region representing intact coating. FIG. 11b is a laser scatter sum image taken across the rectangular region outlined in FIG. 11a. FIG. 11c shows intensity profiles of the laser sum image which clearly illustrate an increase in intensity across the delaminated region, indicating greater scatter from this subsurface defect. The calibration of these images can be used to identify the location and extent of subsurface delaminations in thermal barrier coatings.

There has thus been shown apparatus and method for the detection of defects and microstructural changes in hard translucent materials such as ceramic bulk compositions and ceramic coatings. A variable wavelength laser beam directed onto a specimen surface allows the depth of inspection of the specimen to be varied from the surface to a maximum depth determined by the higher end of the wavelength spectrum. Laser light is reflected by the translucent specimen, with light from small scatter angles directed to a first detector and light from larger scatter angles directed to a second detector. The sum and ratio of the two detector outputs are processed on a real-time basis under the control of a computer to permit very high speed crack defect and microstructural change detection. Greater laser beam wavelengths allow for deeper penetration into the specimen in detecting defects and microstructural changes. The sum signal is more sensitive to surface anamolies and is better, in general, at recognizing and categorizing certain types of defects and microstructural changes. The ratio signal is more sensitive to subsurface defects and microstructural changes. Statistical image processing using a digital image processing approach allows for the quantative discrimination and automatic detection of the presence and distribution of small flaws in a sample while improving the flawed detection reliability. Fiber optics are used to direct the laser beam onto the specimen under investigation in situ without removing the sample from its operating environment.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawing is offered by way of illustration only and not as a limitation. The actual scope of the invention is intended to be defined in the following claims when viewed in their proper perspective based on the prior art.

The embodiments of the invention in which an exclusive property or privilege is claimed are defined as follows:

1. Apparatus for detecting surface and subsurface defects and microstructural changes in translucent ceramic-based materials and coatings, said apparatus comprising:

a tunable laser providing an output beam of high intensity light having a variable wavelength varying between a lower wavelength limit and an upper wavelength limit;

optical means for directing said output beam onto a specimen of a ceramic-based material or coating and for receiving light scattered from the specimen, wherein the specimen is disposed in a machine, said optical means including polarizing means for polarizing said output beam prior to incidence upon the specimen, wherein the wavelength of said output beam varies between said lower and upper wavelength limits allowing said output beam to penetrate from the surface to a given depth of the specimen, and wherein said given depth corresponds to said upper wavelength limit;

first polarization maintaining optical fiber means disposed between said optical means and the specimen for directing the output beam onto the specimen without removing the specimen from said machine, and wherein said polarization maintaining optical fiber means further directs light scattered by the specimen to said optical means to permit distinguishing surface defects and microstructural changes from subsurface defects and microstructural changes by comparing polarization states of the output beam and the light scattered by the specimen;

first detector means for receiving light scattered at small scattering angles from the specimen's surface or subsurface being investigated and providing a first output signal representing light scattered at small scattering angles;

second detector means for receiving light scattered at larger scattering angles from the specimen's surface or subsurface for providing a second output signal representing light scattered at larger scattering angles, wherein larger surface or subsurface defects and microstructural changes exhibit larger scattering angles than the scattering angles from smaller surface or subsurface defects and microstructure changes; and display processing means coupled to said first and second detectors for processing said first and second output signals and visually displaying defects and microstructural changes on and below the surface of the specimen.

2. The apparatus of claim 1 wherein said first polarization maintaining optical fiber means includes first and second inner optical fibers for transmitting the output beam and light scattered by the specimen in opposed directions.

3. The apparatus of claim 2 further comprising second optical fiber means coupling said tunable laser to said optical means for providing the output beam to said optical means.

4. The apparatus of claim 1 wherein said tunable laser is a Ti:Sapphire laser having lower and upper wavelength limits of 700 nm and 1000 nm, respectively.

5. The apparatus of claim 1 wherein said optical means includes a plurality of polarizing beam-splitting cubes, quarter wave plates and positive focusing lenses for separating light scattered from the specimen into light scattered over small angles and light scattered over larger angles from the specimen's surface or subsurface.

6. The apparatus of claim 5 wherein said first detector includes a reflector having a pinhole aperture for passing light scattered over small angles from the specimen's surface or subsurface to said first detector and wherein said reflector directs light scattered over larger angles to said second detector.

7. The apparatus of claim 1 wherein said display processing means includes a video display having a plurality of image producing pixels arranged in a matrix array on said video display, with each pixel representing a particular location on the specimen, and wherein each pixel is assigned a gray scale value in accordance with the values of the first and second output signals of that particular location on the specimen.

8. The apparatus of claim 7 further comprising an automatic defect or microstructural change indication provided when the gray scale value of a pixel or a plurality of adjacent pixels exceeds a predetermined threshold value.

9. The apparatus of claim 1 wherein said display processing means includes means for combining said first and second signals to form a sum of said signals and a ratio of said signals, and wherein the sum of said signals is more sensitive to surface defects and microstructural changes and the ratio of said signals is more sensitive to subsurface defects and microstructural changes.

10. The apparatus of claim 1 further comprising displacement means coupled to the specimen for moving the specimen to permit the output beam to scan the specimen.

* * * * *